(12) United States Patent
Sukovic et al.

(10) Patent No.: US 7,388,941 B2
(45) Date of Patent: Jun. 17, 2008

(54) CT EXTREMITY SCANNER

(75) Inventors: Predrag Sukovic, Birmingham, MI (US); Neal Clinthorne, Ann Arbor, MI (US); Nathaniel Bair, Ann Arbor, MI (US)

(73) Assignee: Xoran Technologies, Inc., Ann Arbor, MI (US)

( * ) Notice: Subject to any disclaimer, the term of this patent is extended or adjusted under 35 U.S.C. 154(b) by 0 days.

(21) Appl. No.: 10/914,627

(22) Filed: Aug. 9, 2004

(65) Prior Publication Data

US 2005/0053185 A1 Mar. 10, 2005

Related U.S. Application Data

(60) Provisional application No. 60/493,405, filed on Aug. 7, 2003.

(51) Int. Cl.
*G01N 23/083* (2006.01)

(52) U.S. Cl. .................................. 378/19; 378/197

(58) Field of Classification Search ................. 378/39, 378/40, 191, 19, 197
See application file for complete search history.

(56) References Cited

U.S. PATENT DOCUMENTS

| | | | | | |
|---|---|---|---|---|---|
| 2,818,510 | A | * | 12/1957 | Verse | 378/189 |
| 3,770,955 | A | * | 11/1973 | Tomita et al. | 378/27 |
| 3,892,967 | A | * | 7/1975 | Howarth et al. | 378/197 |
| 3,908,126 | A | * | 9/1975 | Hudson et al. | 378/39 |
| 3,927,326 | A | * | 12/1975 | Kunne et al. | 378/179 |
| 4,283,629 | A | * | 8/1981 | Habermehl et al. | 378/4 |
| 4,501,009 | A | * | 2/1985 | Abele | 378/19 |
| 4,811,372 | A | * | 3/1989 | Doebert et al. | 378/39 |
| 4,961,208 | A | * | 10/1990 | Okada | 378/18 |
| 5,109,397 | A | * | 4/1992 | Gordon et al. | 378/205 |
| 5,500,884 | A | * | 3/1996 | Guenther et al. | 378/38 |
| 5,511,106 | A | * | 4/1996 | Doebert et al. | 378/146 |
| 5,638,419 | A | * | 6/1997 | Ingwersen | 378/4 |
| 5,642,392 | A | * | 6/1997 | Nakano et al. | 378/38 |
| 5,768,331 | A | * | 6/1998 | Gordon et al. | 378/19 |
| 5,784,428 | A | * | 7/1998 | Schmidt | 378/4 |
| RE36,415 | E | * | 11/1999 | McKenna | 378/4 |
| 6,018,562 | A | * | 1/2000 | Willson | 378/9 |
| 6,212,251 | B1 | * | 4/2001 | Tomura et al. | 378/15 |
| 6,217,214 | B1 | * | 4/2001 | Cabral et al. | 378/196 |
| 6,473,487 | B1 | * | 10/2002 | Le | 378/57 |
| 6,735,274 | B1 | * | 5/2004 | Zahavi et al. | 378/15 |
| 6,940,941 | B2 | * | 9/2005 | Gregerson et al. | 378/4 |
| 6,959,068 | B1 | * | 10/2005 | Sommer | 378/20 |
| 2004/0170254 | A1 | * | 9/2004 | Gregerson et al. | 378/197 |
| 2005/0053186 | A1 | * | 3/2005 | Sukovic et al. | 378/4 |

* cited by examiner

*Primary Examiner*—Edward J. Glick
*Assistant Examiner*—Thomas R. Artman
(74) *Attorney, Agent, or Firm*—Carlson, Gaskey & Olds

(57) ABSTRACT

A CT scanner according to the present invention is particularly adapted for scanning the extremities of a patient. The CT scanner includes an x-ray source and x-ray detector mounted for rotation and translation along an axis parallel to a table for supporting the patient's extremity. The source and detector are mounted opposite one another on an inner circumference of an inner ring. The inner ring is rotatable about the axis within an outer ring mounted on at least one carriage. The carriage is movable parallel to the axis. During scanning, the inner ring rotates within the outer ring while the rings and carriage move along the axis, thereby producing a helical scan of the extremity.

30 Claims, 2 Drawing Sheets

CT EXTREMITY SCANNER

This application claims priority to U.S. Provisional Application Ser. No. 60/493,405 filed Aug. 7, 2003.

BACKGROUND OF THE INVENTION

This invention relates generally to a CT scanner and more particularly to a small CT scanner that is particularly adapted for scanning the extremities of a patient.

CT scanners are generally very large, occupying an entire dedicated room. Thus, doctors must refer patients to hospitals for CT scanning. Also, because of the inconvenience and expense, CT scans are not used for extremities in some cases where a CT scan might be helpful.

SUMMARY OF THE INVENTION

A CT scanner according to the present invention is particularly adapted for scanning the extremities of a patient. The CT scanner is small and easy to use. The CT scanner scans only the desired extremity, not unnecessarily exposing the rest of the patient to x-rays.

The CT scanner includes an x-ray source and x-ray detector mounted for rotation and translation along an axis parallel to a table for supporting the patient's extremity. The source and detector are mounted opposite one another on an inner circumference of an inner ring. The inner ring is rotatable about the axis within an outer ring mounted on at least one carriage. The carriage is movable parallel to the axis. During scanning, the inner ring rotates within the outer ring while the rings and carriage move along the axis, thereby producing a helical scan of the extremity.

BRIEF DESCRIPTION OF THE DRAWINGS

Other advantages of the present invention can be understood by reference to the following detailed description when considered in connection with the accompanying drawings wherein.

DETAILED DESCRIPTION OF THE PREFERRED EMBODIMENTS

Figure 1:
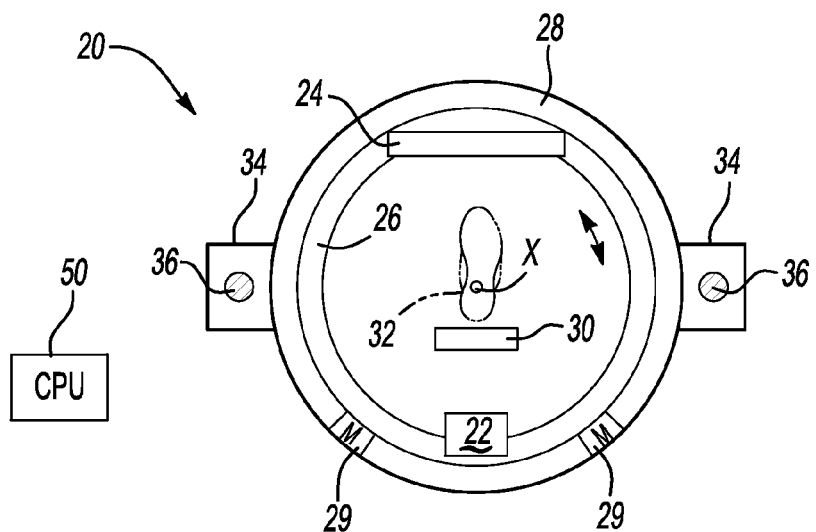
FIG. 1 illustrates an end view of CT scanner according to a first embodiment of the present invention.
Figure 2:
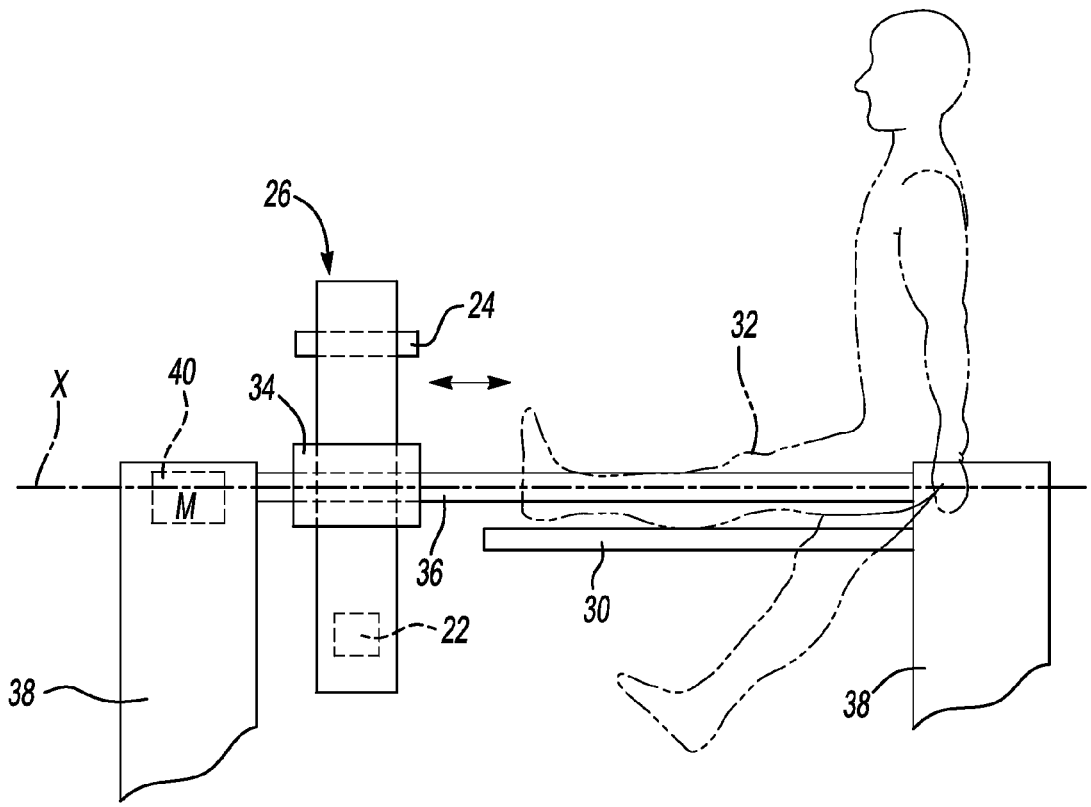
FIG. 2 illustrates a side view of CT scanner according to a first embodiment of the present invention.

A CT scanner 20 according to a first embodiment of the present invention is shown in FIG. 1. The CT scanner 20 is particularly useful for scanning extremities, such as knees, ankles, arms, etc. The CT scanner 20 includes an x-ray source 22 and detector 24 that are mounted on diametrically opposing inner surfaces of an inner ring 26, rotatably mounted within an outer ring 28. Rotation of the inner ring 26 may be accomplished by one or more motors 29 in the outer ring 28. The inner ring 26 has an axis, x, at its center and encircles a radiolucent platform 30 for supporting patients' extremities, such as legs, feet, arms and hands. In this example, the platform 30 supports a leg 32. The source 22 is preferably a cone-beam x-ray source 22 and is directed toward the detector 24 through the axis, x. The outer ring 28 is fixed between a pair of carriages 34, which are movable parallel to the x-axis along a pair of parallel rails 36 supported by opposite stands 38, shown in FIG. 2. The rails 36 threadably engage the carriages 34. Translation along the x-axis is controlled by one or more motors 40 in the stands that rotatably drive one or both of the rails 36. Thus, the source 22 and detector 24 are able to orbit about the x-axis while translating parallel to the x-axis. Alternatively, translation of the outer ring 28, inner ring 26, source 22 and detector 24 along the rails 36 may be accomplished by motors in the carriages 34.

A computer 50 is suitably programmed to control the functions of all of the devices described herein and to perform the image-processing described herein. The computer 50 controls all of the motors in the manner described and receives all of the x-ray images from the detector 24. The computer 50 then generates 3D images of the scanned patient based upon the x-ray images and the known positions of the source 22 and detector 24 at which each x-ray image was taken. Suitable reconstruction algorithms are known and one could be adapted for the present invention by those of skill in the art.

The inner ring 26 may be capable of unlimited rotations about the x-axis if provided with a rotatable electrical coupling (or wireless connection). Alternatively, the inner ring 26 or may alternate between rotating one direction through some fixed angle of rotation and then in the opposite direction through the same fixed angle of rotation, all as the inner ring 26 also translates along the x-axis. For example, the inner ring 26 may rotate 270 degrees clockwise, then 270 degrees counterclockwise, then 270 degrees clockwise, etc. as the inner ring 26 translates along the x-axis. It is not necessary for the inner ring 26 to rotate 360 degrees, only that the computer 50 algorithm that transforms the plurality of images taken by the CT scanner 20 into a three dimensional model knows the angle and the position on the x-axis for each image.

The CT scanner 20 is particularly useful for scanning extremities, such as knees, ankles, arms, etc. Therefore, the inner diameter of the inner ring 26 is preferably between approximately 18" and approximately 24" and more preferably about 18".

Figure 3:
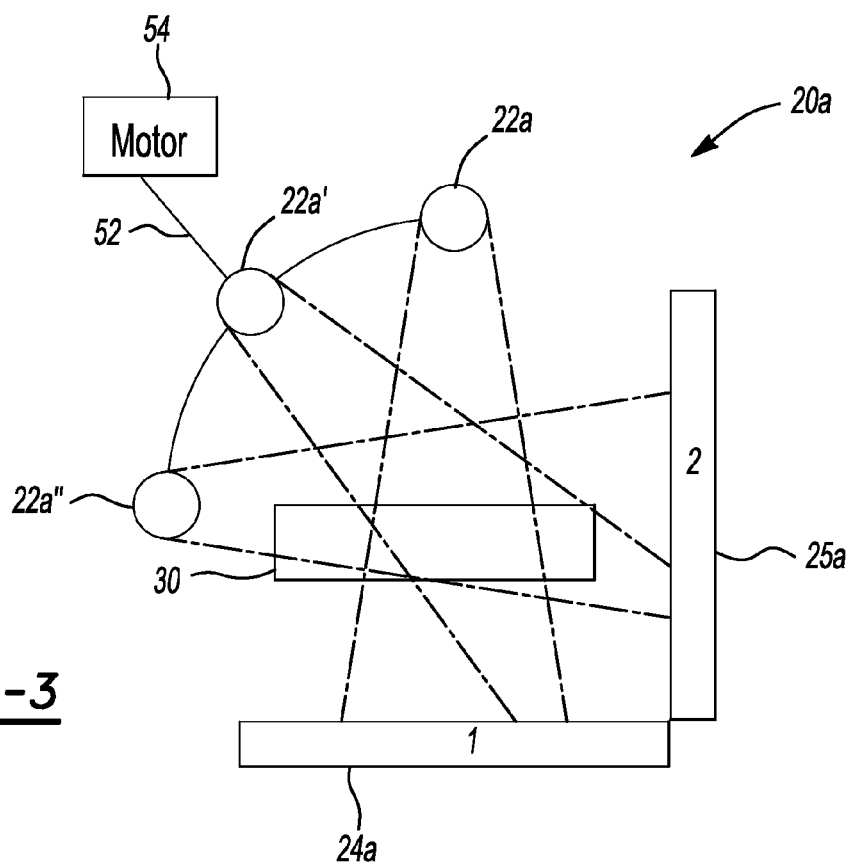
FIG. 3 illustrates an end view of CT scanner according to a second embodiment of the present invention.

FIG. 3 illustrates an alternate extremity CT scanner 20a including a source 22a, similar to the source 22 of the previous embodiment, and a pair of generally perpendicular detectors 24a, 25a. The source 22a is mounted to move generally along an arc such that it initially directs all of its beam onto the horizontal detector 24a, then directs its beam onto both detectors 24a, 25a (shown in position 22a'), then directs all of its beam onto the vertical detector 25a (source shown in position 22a"). The source 22a may be mechanically constrained to move along the arc, such as by a four-bar linkage 52 (shown schematically), and its position controlled by a computer-controlled motor 54. The embodiment of FIG. 3 may also be used effectively for scanning hips.

Figure 4:
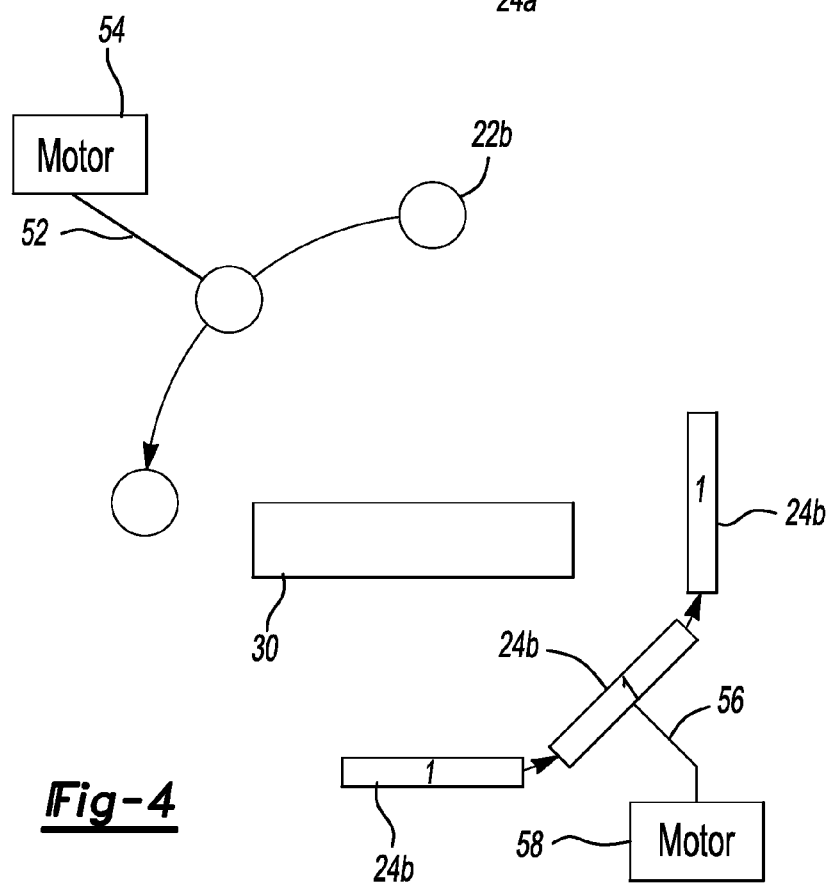
FIG. 4 illustrates an end view of CT scanner according to a third embodiment of the present invention.

Alternatively, as shown in FIG. 4, a single detector 24b can be mounted to move along a complementary arc as the source 22b moves along its arcuate path. Again, the detector 24b may be mechanically constrained to move along the arc, such as by a four-bar linkage 56 (shown schematically), and its position controlled by a computer-controlled motor 58.

Any of the previous three embodiments may be used to scan a joint, such as a knee, that is under consideration for replacement surgery. In a method according to the present invention, a full CT scan of the knee (for example) is first taken in one or two predetermined stationary positions, such as fully extended to 180 degrees and bent to 90 degrees. Then, one or more full CT scans are taken of the knee while moving, so that the kinematics of the knee can be fully modeled. Based upon this complete model, the replacement knee can be placed, oriented and optimized in the computer model prior to surgery. Then, using image-guided surgery, the replacement knee can be implanted in the optimal position and orientation, as determined in the computer model.

Post-operatively, the replacement joint (or other implant) and surrounding tissue can be monitored with any of the above CT scanners. Dual energy sources 22 can be used to distinguish soft-tissue from bone, determine bone density, provide a quantitative measure of bone mass and detect potential infection. The bone growth can be tracked and monitored by comparing the three-dimensional images of the replacement joint and surrounding tissue over time. For example, the bone mass can be shown quantitatively and the new growth can be shown in a different color. It can also be determined whether the bone is growing into pores (or other areas) in the implant. Tracking the three dimensional images of the replacement joint and surrounding tissue over time can also assist doctors in determining if and when the replacement joint needs to be replaced again.

What is claimed is:

1. A CT scanner comprising:
   a horizontal rail supported on a floor;
   a carriage movable along the rail and supported by the rail;
   a ring rotatably mounted to the carriage;
   an x-ray source mounted to the ring; and
   an x-ray detector mounted to the ring opposite the source, a scanning volume within the ring and between the x-ray source and the x-ray detector, the carriage not positioned between the scanning volume and the floor.

2. The CT scanner of claim 1 wherein the ring is an inner ring, the CT scanner further including an outer ring fixedly mounted to the carriage.

3. The CT scanner of claim 2 further including a motor between the inner ring and the outer ring for rotatably driving the inner ring relative to the outer ring.

4. The CT scanner of claim 3 further including a stand supporting the rail.

5. The CT scanner of claim 4 further including a motor translating the carriage along the rail.

6. The CT scanner of claim 5 wherein the rail threadably engages the carriage and the motor rotatably drives the rail relative to the carriage to cause translation of the carriage relative to the rail.

7. The CT scanner of claim 1 wherein the inner diameter of the ring is less than 24".

8. The CT scanner of claim 1 wherein the inner diameter of the ring is between approximately 18" and approximately 24.

9. The CT scanner of claim 1 further including a motor translating the carriage along the rail.

10. The CT scanner of claim 9 wherein the rail threadably engages the carriage and the motor rotatably drives the rail relative to the carriage to cause translation of the carriage relative to the rail.

11. The CT scanner of claim 1 wherein the rail is a first rail and the carriage is a first carriage, the CT scanner further including a second rail parallel to the first rail and a second carriage movable along the second rail, the ring rotatably mounted to the first and second carriages.

12. The CT scanner of claim 1 wherein the carriage is suspended above the ground by the rail without the carriage being directly supported by a floor other than via the rail.

13. The CT scanner of claim 1 wherein the carriage is a first carriage and further including a second carriage, the ring rotatably supported by the second carriage, the ring defining a scanning volume therein, the scanning volume between the first carriage and the second carriage.

14. A CT scanner comprising:
   a generally horizontal rail;
   a first carriage movable along the rail;
   a second carriage;
   a ring rotatably supported by the fist carriage and the second carriage, a scanning volume within the ring, the scanning volume between the first carriage and the second carriage;
   an x-ray source rotatably mounted to the ring; and
   an x-ray detector mounted opposite the source and rotatable with the source.

15. The CT scanner of claim 14 further including an inner ring, the x-ray source mounted to the inner ring, the CT scanner further including an outer ring fixedly mounted to the carriage, the inner ring rotatably mounted to the outer ring.

16. The CT scanner of claim 15 further including a motor between the inner ring and outer ring for rotatably driving the inner ring relative to the outer ring.

17. The CT scanner of claim 16 further including a motor translating the carriage along the rail.

18. The CT scanner of claim 14 wherein the detector is between approximately 18 inches and approximately 24 inches from the source.

19. A CT scanner comprising:
   a horizontal rail;
   a carriage movable along the rail and supported by the rail;
   a pair of stands supporting the rail on the floor, the carriage supported by the rail between the stands;
   a ring rotatably mounted to the carriage;
   an x-ray source mounted to the ring; and
   an x-ray detector mounted to the ring opposite the source.

20. The CT scanner of claim 19 wherein the ring is an inner ring, the CT scanner further including an outer ring fixedly mounted to the carriage.

21. The CT scanner of claim 20 further including a rotation motor between the inner ring and outer ring for rotatably driving the inner ring relative to the outer ring.

22. The CT scanner of claim 21 further including a translation motor translating the carriage along the rail.

23. The CT scanner of claim 22 wherein the rail threadably engages the carriage and the motor rotatably drives the rail relative to the carriage to cause translation of the carriage relative to the rail.

24. The CT scanner of claim 19 wherein the inner diameter of the ring is less than 24".

25. The CT scanner of claim 24 wherein the inner diameter of the ring is between approximately 18" and approximately 24".

26. A CT scanner comprising:
   a horizontal rail;
   a carriage movable along the rail, supported on the rail and threadably engaged by the rail;
   a ring rotatably mounted to the carriage;
   an x-ray source mounted to the ring;
   an x-ray detector mounted to the ring opposite the source; and
   a motor rotatably driving the rail relative to the carriage to cause translation of the carriage relative to the rail.

27. The CT scanner of claim 26 further including a pair of stands supporting the rail therebetween.

28. The CT scanner of claim 26 wherein the ring is an inner ring, the CT scanner further including an outer ring fixedly mounted to the carriage.

29. The CT scanner of claim 28 further including a motor between the inner ring and the outer ring for rotatably driving the inner ring relative to the outer ring.

30. The CT scanner of claim 26 wherein the inner diameter of the ring is less than 24".

* * * * *

UNITED STATES PATENT AND TRADEMARK OFFICE
CERTIFICATE OF CORRECTION

PATENT NO. : 7,388,941 B2  Page 1 of 1
APPLICATION NO. : 10/914627
DATED : June 17, 2008
INVENTOR(S) : Sukovic et al.

It is certified that error appears in the above-identified patent and that said Letters Patent is hereby corrected as shown below:

Claim 8, Column 3, line 46: insert --"-- after 24

Claim 14, Column 4, line 2: "fist" should read as --first--

Signed and Sealed this

Second Day of September, 2008

JON W. DUDAS
*Director of the United States Patent and Trademark Office*